US00PP30973P2

(12) United States Plant Patent
Hansen

(10) Patent No.: US PP30,973 P2
(45) Date of Patent: Oct. 22, 2019

(54) ***PENNISETUM* PLANT NAMED 'PUPPY LOVE'**

(50) Latin Name: *Pennisetum alopecuroides*
Varietal Denomination: Puppy Love

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,482

(22) Filed: Nov. 20, 2018

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
*Assistant Examiner* — Karen M Redden

(57) ABSTRACT

A new and distinct cultivar of ornamental Fountain Grass, *Pennisetum alopecuroides* 'Puppy Love', characterized by vase-shaped habit of medium height and olive-green arching foliage that develops a blush of greyed-purple. Flowering begins in late August with a greyed-purple effective color period of about ten weeks.

1 Drawing Sheet

Botanical classification: *Pennisetum alopecuroides.*
Variety denomination: 'Puppy Love'.

STATEMENT REGARDING PRIOR DISCLOSURES UNDER 37 CFR 1.77(B)(6)

The first publically released photograph of the new plant was on Nov. 28, 2017 when it was pictured on the commercial calendar for Walters Gardens, Inc. The first disclosure, in the form of a sale, was made by Walters Gardens, Inc. on Jul. 9, 2018. Walters Gardens, Inc. obtained the new plant and all information relating thereto, from the inventor. No plants of *Pennisetum* 'Puppy Love' have been sold, in this country or anywhere in the world, nor has any disclosure of the new plant been made, more than one year prior the filing date of this application, and all such sales or disclosures within one year was either derived directly or indirectly from the inventor.

BACKGROUND OF THE NEW PLANT

*Pennisetum alopecuroides* 'Puppy Love', hereinafter also referred to as 'Puppy Love' and "the new plant" is a new and distinct cultivar of Fountain Grass. It is a self-pollinated seedling of *Pennisetum alopecuroides* 'Ginger Love' U.S. Plant Pat. No. 26,442. The single plant selection was discovered by the inventor in the spring of 2012, separated from the remaining seedlings and put through trials and comparisons through the fall of 2017. It was selected for final evaluation in the summer of 2014. The plant has been successfully asexually propagated by division in the spring of 2015 at the same wholesale perennial plant nursery in Zealand, Mich. and found to produce identical plants that maintain the unique characteristics of the original plant. The plant is stable and reproduces true to type in successive generations of asexual reproduction.

BRIEF SUMMARY OF THE NEW PLANT

*Pennisetum* 'Puppy Love' differs from the female parent and all other fountain grass known to the inventor. The nearest comparisons to *Pennisetum* 'Puppy Love' are: 'Ginger Love', 'Red Head' (not patented) and 'Hameln' (not patented). 'Ginger Love' is slightly taller in side by side comparisons, and is more outright in flower spikes, but the flowers on the new plant are darker greyed-purple rather than the reddish coloration of 'Ginger Love' and the foliage of the new plant has a tendency to develop burgundy tinting unlike 'Ginger Love'. 'Hameln' is slightly shorter than the new plant with more golden flower heads in the fall. 'Red Head' has a much taller habit and produces longer panicles of a more reddish coloration than the new plant and the foliage of 'Red Head' turns yellowish in the fall.

'Puppy Love' differs from its female parent as well as all other *Pennisetum* known to the applicant by the following unique traits:

1. The plant develops into a medium height vase-shaped habit.
2. The medium green foliage is gracefully arching and develops a greyed-purple tinting later in the season.
3. Blooms of greyed-purple starts in mid-August with the plumes persisting into fall, effective for about ten weeks.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
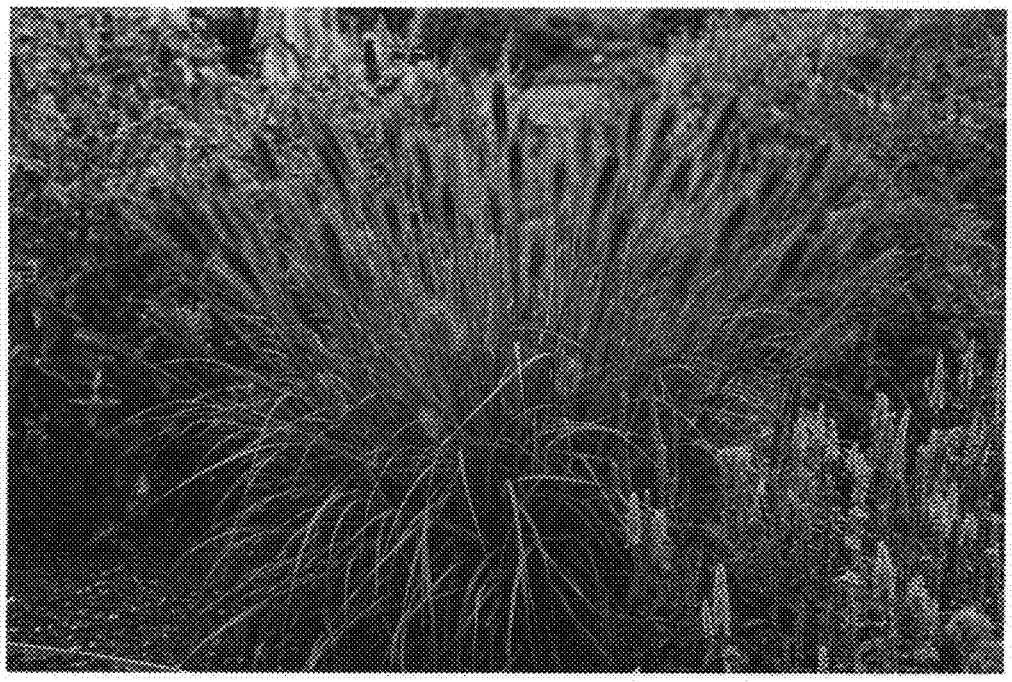
FIG. 1 shows a four-year-old plant in the landscape in early flowering stage.
Figure 2:
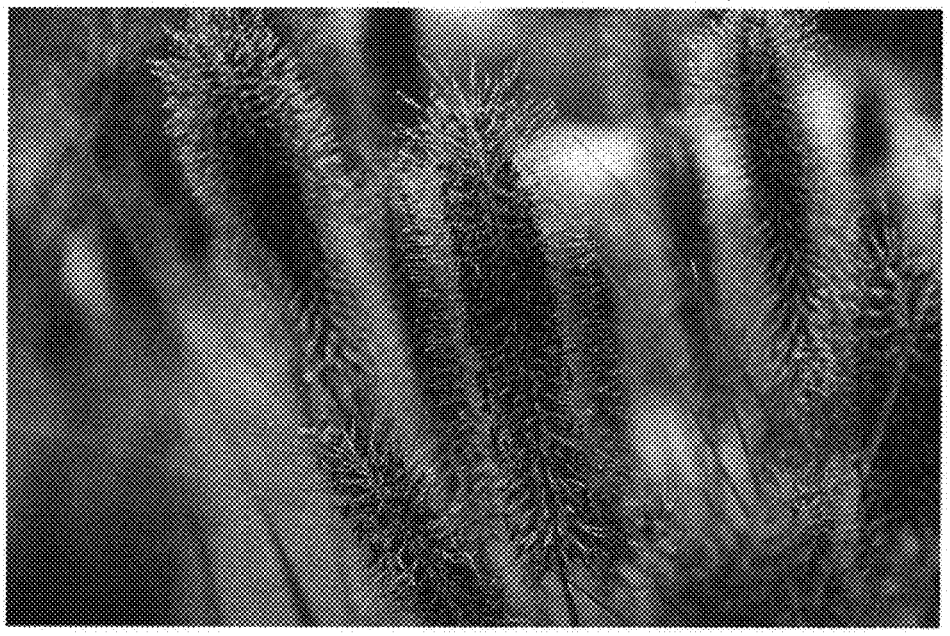
FIG. 2 shows a close up of the flowers.

The following descriptions and color references are based on the 2015 edition of The Royal Horticultural Society Colour Chart except where common dictionary terms are used. The new plant, *Pennisetum* 'Puppy Love', has not been observed under all possible environments. The phenotype may vary slightly with different environmental conditions, such as temperature, light, fertility, moisture and maturity levels, but without any change in the genotype. The following observations and size descriptions are of a four-year old plant in a display garden in Zealand, Mich. in full sun with supplemental water and fertilizer.

Parentage: The female parent is *Pennisetum* 'Ginger Love'; most likely 'Ginger Love' was the male parent.

Propagation method: Division of the rhizomes in early spring;

Time to finishing in a 65 cm pot: Three months;

Rooting habit: Normal, coarsely branching; color variable depending on soil types, nearest RHS 158D;

Plant description:

Plant shape and habit: Hardy, herbaceous, perennial grass forming tightly rhizomatous mound of arching foliage, with upright vase-shaped culms topped with finely textured airy inflorescence;

Foliage: Cauline and basal; linear; two-ranked; glabrous, flat, erect to arcuate toward apices, sheathed from node of attachment to ligule; narrowly acute apex; base sheath; margin entire; deciduous but persist through winter; lustrous adaxial and matte abaxial;

Foliage size: To about 51.0 cm long and about 8.0 mm wide, averaging about 45 cm long and about 8 mm wide;

Sheath: Overlapping margins in upper leaves, not overlapping in lower leaves; to about 14.0 cm long, average about 12.5 cm long;

Leaf color: Adaxial nearest RHS 137A with blushing accents of between RHS 187B and RHS N186C; abaxial nearest RHS 137B;

Veins: Parallel; not obvious; colors identical to surrounding leaf on both the top and bottom; without prominent midrib;

Culm: Erect, terete, stiff; completely enclosed by leaf sheath in distal portion and partially exposed in proximal portion; to about 97.5 cm tall, about 5.0 mm wide at base, average about 92 cm tall and 5.0 mm diameter;

Inflorescence: Usually one panicle per culm; to about 97.5 cm tall;

Flower effective period: Beginning mid-August and continuing to produce young flower spikes into late September; individual spikes effective for up to about 10 weeks; No fragrance detected;

Flower: Perfect; incomplete; terminal bristled pubescent; about 175 flowers covering the terminal 14.0 cm of the rachis; about 5.2 cm wide; dehiscent;

Flower fragrance: No fragrance detected;

Flower attitude: Outright to slightly upright;

Rachis: Up to 14.0 cm long; stiff; upright; color nearest RHS 137B;

Individual florets size: About 9.0 mm long and 2.5 mm across;

Rachilla: Stiff, cylindrical; to about 4.0 mm long and 0.3 mm diameter; color nearest RHS 137C;

Lemma: (Outer bract) ovate to lanceolate; acute apex and truncate base; glabrous; glaucous; about 3.0 mm long and 1.0 mm wide at base; color abaxial and adaxial base nearest RHS 138B, distal two-thirds nearest RHS 187A;

Glumes or palea: Two; lanceolate; narrowly acute apex and truncate base; glabrous, glaucous; about 7.0 mm long and 2.0 mm wide toward center; color abaxial and adaxial distal one-half nearest RHS 187A, abaxial and adaxial base nearest RHS 145B with veins nearest RHS 187A;

Bristles: Size variable, 2.0 mm to 25.0 mm long and about 0.1 mm diameter; flexible but stiff;

Bristle color: Nearest N186B;

Gynoecium: Single; to about 9.0 mm long;

Stigma: Divergent bifid; plumose; protruding 1.0 to 2.0 mm from glume and about 1.0 to 2.0 mm long; color nearest RHS NN155B;

Style: About 4.0 mm long; color nearest RHS NN155B;

Ovary: Globose; about 0.5 mm diameter; color nearest RHS 193C;

Androecium: Three;

Filaments: Fine, hair-like, nearest RHS NN155B, less than 1 mm diameter and about 2.0 mm long;

Anthers: About 2.0 to 3.0 mm long and about 1.0 mm wide, closest to RHS 163A;

Pollen: Elliptical, less than 0.1 mm long, nearest RHS N25B;

Fruit: Caryopsis; slightly flattened ellipsoid with pointed apex and base, about 2.5 mm long and 1.2 mm wide, nearest RHS 199B;

Hardiness, pest and disease resistance: The plant grows best with plenty of moisture and adequate drainage, but is able to tolerate some drought when mature. Hardiness at least from USDA zone 5 through 9. Disease and pest resistance beyond what is typical of that of other Fountain Grass has not been observed.

I claim:

1. A new and distinct cultivar of ornamental *Pennisetum alopecuroides* plant named 'Puppy Love' as herein described and illustrated.

* * * * *